(12) United States Patent
Stowasser

(10) Patent No.: US 11,244,433 B2
(45) Date of Patent: Feb. 8, 2022

(54) MEDICAL X-RAY DEVICES AND METHODS FOR OPERATING MEDICAL X-RAY DEVICES

(71) Applicant: Siemens Healthcare GmbH, Erlangen (DE)

(72) Inventor: Boris Stowasser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 219 days.

(21) Appl. No.: 16/426,326

(22) Filed: May 30, 2019

(65) Prior Publication Data

US 2019/0378256 A1 Dec. 12, 2019

(30) Foreign Application Priority Data

Jun. 7, 2018 (EP) .................................... 18176498

(51) Int. Cl.
*G06T 5/50* (2006.01)
*G06T 7/254* (2017.01)
(Continued)

(52) U.S. Cl.
CPC .............. *G06T 5/50* (2013.01); *A61B 6/5235* (2013.01); *A61B 6/5264* (2013.01);
(Continued)

(58) Field of Classification Search
CPC .. G06T 5/50; G06T 7/254; G06T 7/97; G06T 7/0016; G06T 2207/10116;
(Continued)

(56) References Cited

U.S. PATENT DOCUMENTS 3,974,386 A * 8/1976 Mistretta ................. A61B 6/405
378/98.11
4,881,124 A * 11/1989 Yokouchi ............. H04N 5/3205
378/98.2

(Continued)

FOREIGN PATENT DOCUMENTS

DE 102006037969 * 2/2008
JP 2010279594 A 12/2010

OTHER PUBLICATIONS

European Search Report for European Patent Application No. 18176498.6-1124 dated Nov. 6, 2018.

*Primary Examiner* — Shaghayegh Azima
(74) *Attorney, Agent, or Firm* — Lempia Summerfield Katz LLC

(57) ABSTRACT

Methods are provided for operating a medical X-ray device to improve the image quality of an X-ray examination. In one example, the method includes recording at least one first X-ray image of a body region as a mask image; providing a first subsequent image and recording a second X-ray image of the body region, wherein the second X-ray image represents the body region at a later recording time than the first subsequent image; determining a degree of deviation relating to a deviation between the first subsequent image and the second X-ray image; determining an averaging amount in dependence on the degree of deviation; generating a second subsequent image from the second X-ray image or from the first subsequent image together with the second X-ray image, wherein the averaging amount specifies the proportions in which the first subsequent image and the second X-ray image are mixed; and forming an overall image from the mask image and the second subsequent image.

19 Claims, 3 Drawing Sheets

(51) Int. Cl.
*G06T 7/00* (2017.01)
*A61B 6/00* (2006.01)

(52) U.S. Cl.
CPC ............ *G06T 7/0016* (2013.01); *G06T 7/254* (2017.01); *G06T 7/97* (2017.01); *G06T 2207/10116* (2013.01); *G06T 2207/20216* (2013.01); *G06T 2207/20224* (2013.01)

(58) Field of Classification Search
CPC . G06T 2207/20216; G06T 2207/20224; A61B 6/5235; A61B 6/5247; A61B 6/5264
See application file for complete search history.

(56) References Cited

U.S. PATENT DOCUMENTS

| | | | | |
|---|---|---|---|---|
| 5,091,925 A * | 2/1992 | Haendle | ................... | H04N 5/32 348/607 |
| 6,314,160 B1 * | 11/2001 | Dhawale | ................. | H04N 5/325 378/98.2 |
| 10,758,199 B2 * | 9/2020 | Hayashi | ................ | A61M 5/007 |
| 2008/0137935 A1 * | 6/2008 | Spahn | ....................... | G06T 5/50 382/132 |
| 2009/0076369 A1 * | 3/2009 | Mistretta | ................... | G06T 7/00 600/407 |
| 2009/0202129 A1 * | 8/2009 | Omi | ......................... | H04N 5/32 382/132 |
| 2010/0142792 A1 * | 6/2010 | Sakaguchi | ................ | G06T 5/50 382/132 |
| 2012/0155237 A1 | 6/2012 | Takahashi | | |
| 2013/0070062 A1 * | 3/2013 | Fouras | ................... | A61B 6/486 348/50 |
| 2013/0077750 A1 * | 3/2013 | Yabugami | ............... | A61B 6/481 378/62 |
| 2018/0101948 A1 * | 4/2018 | Yu | ......................... | G06T 7/0012 |
| 2018/0204322 A1 * | 7/2018 | Zhou | ..................... | G06T 11/006 |
| 2018/0242939 A1 * | 8/2018 | Kang | ...................... | A61B 6/482 |
| 2021/0280775 A1 * | 9/2021 | Buhrman | ................ | H01L 43/04 |

* cited by examiner

MEDICAL X-RAY DEVICES AND METHODS FOR OPERATING MEDICAL X-RAY DEVICES

The present patent document claims the benefit of European Patent Application No. EP 18176498.6, filed Jun. 7, 2018, which is also hereby incorporated by reference.

TECHNICAL FIELD

The disclosure relates to methods for operating a medical X-ray device. A second aspect of the disclosure relates to medical X-ray devices.

BACKGROUND

Known from the prior art are methods for performing an X-ray examination, (e.g., fluoroscopy), with which a plurality of X-ray images is recorded in succession in order to detect a temporal change at a body region to be examined. Such a temporal change relates to a movement at the body region. Such a movement may be due to the administration of a contrast agent to a body fluid flowing through the body region. In other words, the contrast agent may be injected in the body region to be examined and a propagation of the contrast agent may be examined using the plurality of X-ray images. To this end, the contrast agent may be selected to be visible in the X-ray images. For example, the contrast agent is injected into a vessel, (e.g., a blood vessel), of the body region. In other words, a vascular tree of the body region may be visualized thereby. Such methods may be summarized under the technical term (digital) subtraction angiography (DSA).

Alternatively, the movement of a medical object, (e.g., a guidewire or a catheter), may be detected by the plurality of X-ray images. For example, a user of the medical X-ray device moves or places the medical object on or in the body region. This process may be monitored by the X-ray examination. Such methods are also known by the technical term "roadmap".

In order to achieve better visibility of the medical object or the contrast agent, in a first phase of the X-ray examination, a so-called mask image may be created in which the body region is detected statically. Herein, advantageously, a static mask image of the body region is created before the movement occurs. Specifically, this first phase or the recording of the mask image may take place before the contrast agent is injected or the medical object is moved to the body region.

In this case, the movement may only take place at the start or after the start of a second phase of the X-ray examination. In this second phase, the movement is visualized by the plurality of successive X-ray images as described above. To enable a better overview of the body region or the movement, respective overall images of the second phase may in each case be formed from one image of the plurality of X-ray images and the mask image. For example, each of the plurality of X-ray images recorded during the second phase are developed together with the mask image to form an overall image. Because the X-ray images of the second phase are recorded after the first X-ray images or the mask image, these are referred to as second X-ray images.

For example, a respective overall image may be formed by subtracting the mask image from a respective one of the second X-ray images. In other words, during the X-ray examination, the mask image may be subtracted from each of the second X-ray images. Subtraction of the mask image enables a static portion of the image information to be removed from the respective second X-ray images thus rendering the movement even more visible.

During the recording of X-ray images, there is the possibility of the occurrence of statistical image noise. This image noise may be described mathematically by a variance. The lower an X-ray dose during the recording of the respective X-ray image, the more significant the image noise or the variance. In particular, the signal-to-noise ratio deteriorates as the dose decreases. Hence, there is a conflict of interest between the highest possible image quality and the lowest possible dose. Herein, it has been found to be advantageous to record a plurality of X-ray images in the first phase and average them arithmetically to form the mask image. In mathematical terms, the variance of the averaged mask image is indirectly proportional to the number of X-ray images used in the averaging.

However, in the second phase of the X-ray examination, averaging using a plurality of X-ray images is not necessarily advisable because, in the event of a movement, the contrast is reduced by the averaging. For example, the movement is averaged out of the second X-ray images. If a respective overall image is now formed from a respective second X-ray image and the mask image, the achievable image quality is limited by the noise of the respective second X-ray image. In the example given, subtraction imaging, with which the mask image is subtracted from the respective second X-ray image, this may be explained mathematically by way of example. In the case of the subtraction of the mask image from the respective second X-ray image, the respective variances of the mask image and the respective second X-ray image are added together. In practice, this means the maximum achievable image quality is limited by the image noise of the second X-ray image, regardless of how well the noise is averaged out of the mask image.

SUMMARY AND DESCRIPTION

It is the object of the present disclosure to improve image quality in such an X-ray examination compared to the prior art.

The scope of the present disclosure is defined solely by the appended claims and is not affected to any degree by the statements within this summary. The present embodiments may obviate one or more of the drawbacks or limitations in the related art.

A first aspect of the disclosure is based on a method for operating a medical X-ray device during an X-ray examination. The method includes: recording at least one first X-ray image of a body region as a mask image; providing a first subsequent image and recording a second X-ray image of the body region, wherein the second X-ray image represents the body region at a later recording time than the first subsequent image; determining a degree of deviation relating to a deviation between the first subsequent image and the second X-ray image, determining an averaging amount in dependence on the degree of deviation according to a predetermined rule; generating a second subsequent image from the second X-ray image or from the first subsequent image together with the second X-ray image, wherein the averaging amount specifies the proportions in which the first subsequent image and the second X-ray image are mixed thereby, and forming an overall image from the mask image and the second subsequent image.

In the recording of the at least one first X-ray image, a first X-ray image or a plurality of first X-ray images is recorded for the mask image. In the case of a plurality of first X-ray images, these may be averaged to form the mask image. In other words, the recording may include the formation of the mask image from the at least one first X-ray image. In particular, the recording may include the averaging of a plurality of first X-ray images to form the mask image. The recording of the at least one first X-ray image may be referred to as the first phase of the X-ray examination. The formation of the mask image or the averaging of the plurality of first X-ray images may also be understood to be part of the first phase.

The provision of the first subsequent image and the recording of the second X-ray image may be understood to be part of a second phase of the X-ray examination. In this second phase of the X-ray examination, a movement at the body region such as the movement of a medical object (e.g., a guidewire or catheter) or a contrast agent, may be examined during the X-ray examination. The second phase takes place after the time of the first phase, e.g., directly following the first phase. The aforementioned at least one first X-ray image is designated such because it is recorded in the first phase; similarly, second X-ray images are designated such this because they are recorded during the second phase. The first subsequent image may be a further second X-ray image recorded during the provision. Alternatively, the first subsequent image may be averaged from a plurality of second X-ray images. This averaging may be understood to be part of the provision. In particular, the first subsequent image is generated and provided by averaging a plurality of second X-ray images. All of the images in the plurality of second X-ray images used for this advantageously represent the body region at an earlier recording time than the second subsequent image. In other words, all of the images in the plurality of second X-ray images for providing the first subsequent image are recorded at a time before the second X-ray image. If only one single further second X-ray image is provided as the first subsequent image, this is recorded before the second X-ray image.

The recording time of the first subsequent image may correspond to the recording time of the single further second X-ray image, which is provided as the first subsequent image. If the first subsequent image is provided from a plurality of second X-ray images, the recording time of the first subsequent image may correspond to an averaged recording time for the plurality of second X-ray images or a recording time for the most current of the plurality of X-ray images. Self-evidently, the recording time of the second X-ray image corresponds to its recording time.

To determine the degree of deviation, respective intensities of the first subsequent image and the second X-ray image may be evaluated. In particular, the first subsequent image and the second X-ray image relate to grayscale images with grayscales representing respective intensities. The intensity of a radiation intensity detected by a detector of the medical X-ray device may be represented by the grayscales. Herein, the degree of deviation may be determined in a particularly simple manner by comparing respective gray values of the first subsequent image and the second X-ray image. For example, the degree of deviation is determined by subtracting the respective gray values of the first and the second X-ray image. In addition, an amount of a result of the subtraction may be determined to determine the degree of deviation. In other words, the degree of deviation may be formed from the amount of a difference between the respective gray values of the first and the second X-ray image.

The predetermined rule for determining the averaging amount may include an allocation table. The allocation table may assign a specified value for the averaging amount to each possible value of the degree of deviation. Alternatively, or additionally, the predetermined rule may include a distribution function. The distribution function provides a mathematical relationship between the degree of deviation and the averaging amount. The distribution function enables the averaging amount to be determined in dependence on the degree of deviation.

The first subsequent image and the second X-ray image are mixed in dependence on the averaging amount in order to generate the second subsequent image. Hence, the second subsequent image may be generated by averaging the first subsequent image and the second X-ray image or by providing the second X-ray image. Whether and to what degree averaging takes place is specified by the averaging amount. For example, the averaging amount may specify that the second subsequent image is generated exclusively from the second X-ray image. In one example, no averaging takes place. Alternatively, the averaging amount may specify that the second subsequent image is generated from the second X-ray image and the first subsequent image, wherein in this case a degree of averaging is specified by the averaging amount. Herein, the averaging of the first subsequent image and the second X-ray image during the generation of the second subsequent image in particular relates to respective intensity values of radiation intensity detected in each case, (e.g., the respective gray values), of the first subsequent image and the second X-ray image. The mixing may be performed by averaging the intensity values. Herein, the averaging amount may be understood to be a weighting factor during the averaging of the intensity values. In other words, the respective intensity values or the respective grayscales are averaged during the generation of the second subsequent image. Herein, the averaging amount may specify a weighting ratio. Hence, the second subsequent image may be understood to be a post-processed X-ray image of the second phase.

During the formation of the overall image, this image may be assembled from the mask image and the second subsequent image. For example, the mask image and the second subsequent image may be superimposed to form the overall image. Alternatively, the mask image is subtracted from the second subsequent image. An image quality of the overall image may be particularly high because it is possible achieve averaging of the mask image and averaging of the second subsequent image. In this way, the respective image noise of both the mask image and the second subsequent image may first be reduced independently in each case before the respective image noise of the mask image and the second subsequent image in the overall image are added together. The degree of deviation and the averaging amount dependent thereupon provide that the averaging of the first subsequent image and the second X-ray image only takes place when a deviation between the first subsequent image and the second X-ray image exceeds a predetermined degree. This enables loss of contrast due to the averaging to be counteracted. The deviation between the first subsequent image and the second X-ray image may result from a movement at the body region.

According to a further embodiment, during the generation of the second subsequent image, respective intensity values of corresponding pixels of the first subsequent image and the second X-ray image are mixed in dependence on the averaging amount. The intensity values may in each case be represented by grayscales or gray values of the respective subsequent image. The intensity values relate to a respective detected radiation intensity at the detector of the X-ray device. Corresponding pixels of the first subsequent image and the second X-ray image may be pixels with the same coordinates. In other words, the intensity values of the respective pixels of the first subsequent image and the second X-ray image are mixed or averaged with the same coordinates in each case. This enables the image noise of the individual pixels to be at least partially averaged out.

According to a further embodiment, the degree of deviation characterizes a movement at the body region that occurs in a period between a recording time of the first subsequent image and a recording time of the second X-ray image. This movement at the body region relates to the movement of the medical object or the contrast agent. The more pronounced the movement, the greater the degree of deviation. In other words, the degree of deviation may be a measure of the intensity of the movement. The more pronounced the movement at the body region, the greater the value determined for the degree of deviation may be. The fact that the movement at the body region is characterized by the degree of deviation enables averaging of the first subsequent image and the second X-ray image on the generation of the second subsequent image to be reduced in dependence on the movement.

According to a further embodiment, the averaging amount defines the proportion in which the second subsequent image corresponds to the second X-ray image. In particular, the fixed averaging amount defines what proportion of the intensity values or the gray values of the second subsequent image correspond to the second X-ray image. For example, the averaging amount may define that the second subsequent image corresponds completely to the second X-ray image. In this case, no averaging is performed. Alternatively, the averaging amount may define that averaging is performed and the second subsequent image corresponds to the second X-ray image in a proportion defined by the averaging amount. Alternatively, or additionally, the averaging amount may define the proportion in which the first subsequent image is mixed into the second X-ray image during the generation of the second subsequent image. The mixing or averaging according to the averaging amount enables this to be influenced and adapted particularly well.

According to a further embodiment, the averaging amount defines the proportion in which a pixel intensity of a pixel of the second subsequent image corresponds to a pixel intensity of a corresponding pixel of the second X-ray image. Corresponding pixels of the second subsequent image, the first subsequent image and the second X-ray image may be respective pixels with the same coordinates. Alternatively, or additionally, the averaging amount may define the proportion in which the pixel intensity of a pixel of the second subsequent image corresponds to a pixel intensity of a corresponding pixel of the first subsequent image. For example, the pixel intensity of a pixel of the second subsequent image corresponds with a proportion defined by the averaging amount to the pixel intensity of the corresponding pixel of the second X-ray image and with a further proportion defined by the averaging amount to the pixel intensity of the corresponding pixel of the first subsequent image. Herein, the proportion and the further proportion together may produce one.

According to a further embodiment, the acts of determining a degree of deviation, determining an averaging amount, and generating a second subsequent image are carried out separately in each case for different regions, (e.g., individual pixels), of the second subsequent image. In other words, a respective degree of deviation and a respective averaging amount are determined for the respective regions, e.g., the individual pixels. The generation of the second subsequent image from the second X-ray image or the first subsequent image and the second X-ray image is then performed region-by-region for the different regions, (e.g., the individual pixels), of the second subsequent image separately in each case. In particular, the degree of deviation characterizes the movement in each of the different regions, (e.g., individual pixels), separately in each case and, on the basis thereof, image information in the different regions of the second subsequent image is mixed or averaged separately in each case from the first subsequent image and the second X-ray image. This enables the image quality to be further improved.

According to a further embodiment, the first subsequent image provided is one that was previously formed (similarly to the acts of providing a first subsequent image and recording a second X-ray image of the body region, determining a degree of deviation, determining an averaging amount, and generating a second subsequent image) from a further first subsequent image and a further second X-ray image. In other words, the first subsequent image itself may be formed by mixing a plurality of images, namely the further first subsequent image and the further second X-ray image. Hence, this advantageously relates to an iterative method in which a new subsequent image is formed either exclusively from a new second X-ray image or from the new second X-ray image and a previous subsequent image. Herein, a respective averaging amount, which is in turn dependent on a respective degree of deviation, determines in order to specify a proportion in which the previous subsequent image is mixed into the new second X-ray image to form the new subsequent image. For example, a value range may specify an averaging amount so that the new second X-ray image is mixed into the new subsequent image in a percentage of 20% to 100%. This enables the averaging to be performed iteratively over a plurality of subsequent images. Herein, the newer the respective image, the greater the contribution of the plurality of subsequent images to the current subsequent image.

According to a further embodiment, the determination of the averaging amount is performed using the predetermined rule by a distribution function, which is a function of the degree of deviation, wherein the distribution function is provided in dependence on an operating parameter of the X-ray device. The operating parameter may relate to an acceleration voltage, a dose, a frequency, or any other parameter of the X-ray device. The distribution function may be provided in dependence on a plurality of operating parameters of the X-ray device. For example, the distribution function is selected in dependence on the operating parameter from multiple distribution functions stored in the X-ray device. Alternatively, the distribution functions may be formed based on the operating parameter. Herein, one or more points of the distribution function may be calculated from the operating parameter and a universal pattern of the distribution function, which may be specified, fitted, or configured to the calculated point or points. This enables the determination of the degree of deviation to be improved in that the movement may be characterized in a more targeted manner.

According to a further embodiment, a noise amplitude is determined in the first subsequent image and/or the second X-ray image and a threshold value for the distribution function is defined in dependence on the noise amplitude. In particular, the noise amplitude may be understood to be an operating parameter of the X-ray device. The threshold value may characterize whether a deviation determined in the context of the degree of deviation may be attributed to an image noise or a movement. For example, for values of the degree of deviation that are smaller than the threshold value, the averaging amount is determined such that a greater degree of averaging is used during the generation of the second subsequent image than for values of the degree of deviation that are greater than the threshold value. This provides that the image noise is reduced, but in the case of a movement, the averaging is reduced or omitted.

According to a further embodiment, during the formation of the overall image, the mask image and the second subsequent image are subtracted from one another. In other words, the overall image is generated by subtracting the mask image from the second subsequent image. This enables the movement, which may be examined by the X-ray examination, to be visualized particularly well by subtraction of the static image content.

According to a further embodiment, during the recording of the at least one first X-ray image, a plurality of first X-ray images is recorded and averaged according to a recurrence formula to generate the mask image. In other words, the averaging of the plurality of first X-ray image is not performed by adding the plurality of X-ray images and subsequently dividing by the number, but recursively by successive averaging from image to image. This may improve an image quality as early as the creation of the mask image.

According to a further embodiment, during the generation of the mask image, the same formula is used to mix the plurality of first X-ray images as during the generation of the second subsequent image according to the act of generating a second subsequent image for mixing the first subsequent image and the second X-ray image. In other words, the plurality of first X-ray images for generating the mask image is mixed or averaged by the same formula as the first subsequent image and the second X-ray image to generate the second subsequent image. This particularly advantageously enables switching between the first phase and the second phase because the same formula is used in both phases.

According to a further embodiment, a change in position of a medical object between the first subsequent image and the second X-ray image is determined and respective object regions of the first subsequent image and/or the second X-ray image are mixed using motion compensation, wherein, in the respective object regions, the medical object is detected in the first subsequent image and the second X-ray image.

The medical object may be a guidewire or a catheter. To this end, first the respective object regions may be determined in the first subsequent image and the second X-ray image. The change in position of the medical object may be determined by comparing the coordinates of the respective object regions. The motion compensation may shift and/or rotate the object region of the first subsequent image such that maximum overlapping with the object region of the second subsequent image is achieved. This maximum overlapping may be determined by the least squares method. This may be used to define an overall degree of deviation between the respective object regions. In the example, this overall degree of deviation may be reduced by shifting the object region of the first subsequent image until a (e.g., absolute) minimum of the overall degree of deviation is achieved. The object regions may then be mixed. Herein, in a further object region, the second subsequent image is generated by mixing or averaging the object region of the first subsequent image and the object region of the second X-ray image. The further object region of the second subsequent image may have the same coordinates as the object region of the second X-ray image. This results in improved contrast in a region around the medical object. This enables a movement of the medical object to be depicted with improved image quality.

A second aspect of the disclosure relates to a medical X-ray device for performing an X-ray examination, with: a recording unit for recording at least one first X-ray image of a body region as a mask image and for recording a second X-ray image of the body region; a providing unit for providing a first subsequent image of the body region, wherein the second X-ray image represents the body region at a later recording time than the first subsequent image; a first determining unit for determining a degree of deviation relating to a deviation between the first subsequent image and the second X-ray image; a second determining unit for determining an averaging amount in dependence on the degree of deviation according to a predetermined rule; a generating unit for generating a second subsequent image from the second X-ray image or from the first subsequent image together with the second X-ray image, wherein the averaging amount specifies the proportions in which the first subsequent image and the second X-ray image are to be mixed thereby by the generating unit; and a combining unit for forming an overall image from the mask image and the second subsequent image.

The medical X-ray device may be configured to carry out a method as described above. Hence, the features of the method and developments of the method apply analogously to the medical X-ray device and develop the device analogously.

BRIEF DESCRIPTION OF THE DRAWINGS

The disclosure is now explained in more detail with reference to several drawings.

DETAILED DESCRIPTION

Figure 1:
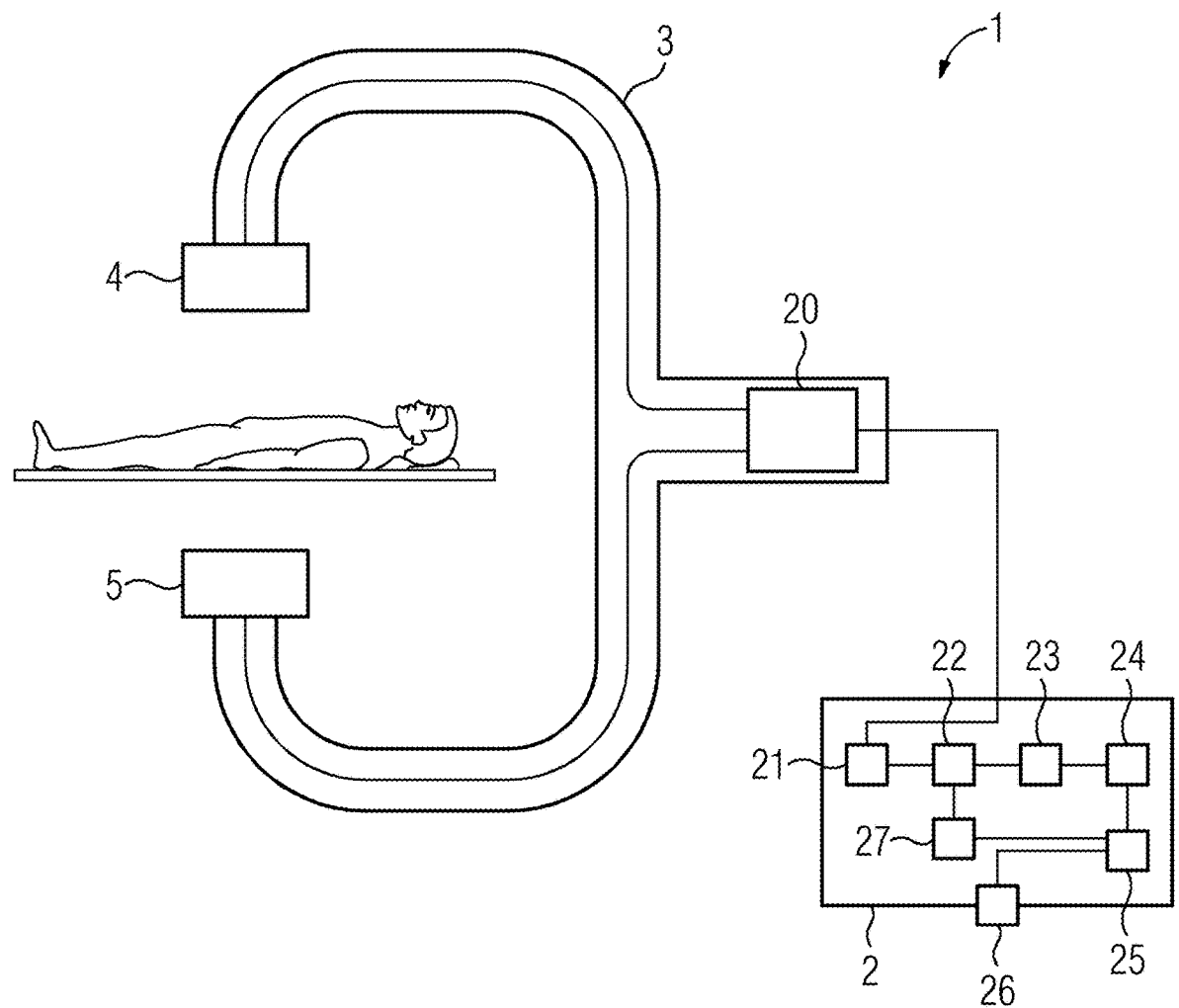
FIG. 1 depicts a block diagram example of a medical X-ray device.

FIG. 1 depicts a medical X-ray device 1, a so-called C-arm X-ray device. The X-ray device 1 includes an X-ray apparatus 3 and a computing apparatus 2. In this example, the X-ray apparatus 3 includes an X-ray source 4 and a detector 5, (an X-ray detector). The X-ray apparatus 3 also includes a recording apparatus 20 for recording X-ray images. In this example, the computing apparatus 2 includes a providing unit 21, a first determining unit 22, a second determining unit 23, a generating unit 24, a combining unit 25, and an output unit 26. The output unit 26 is embodied to output an image sequence of processed X-ray images.

Figure 2:
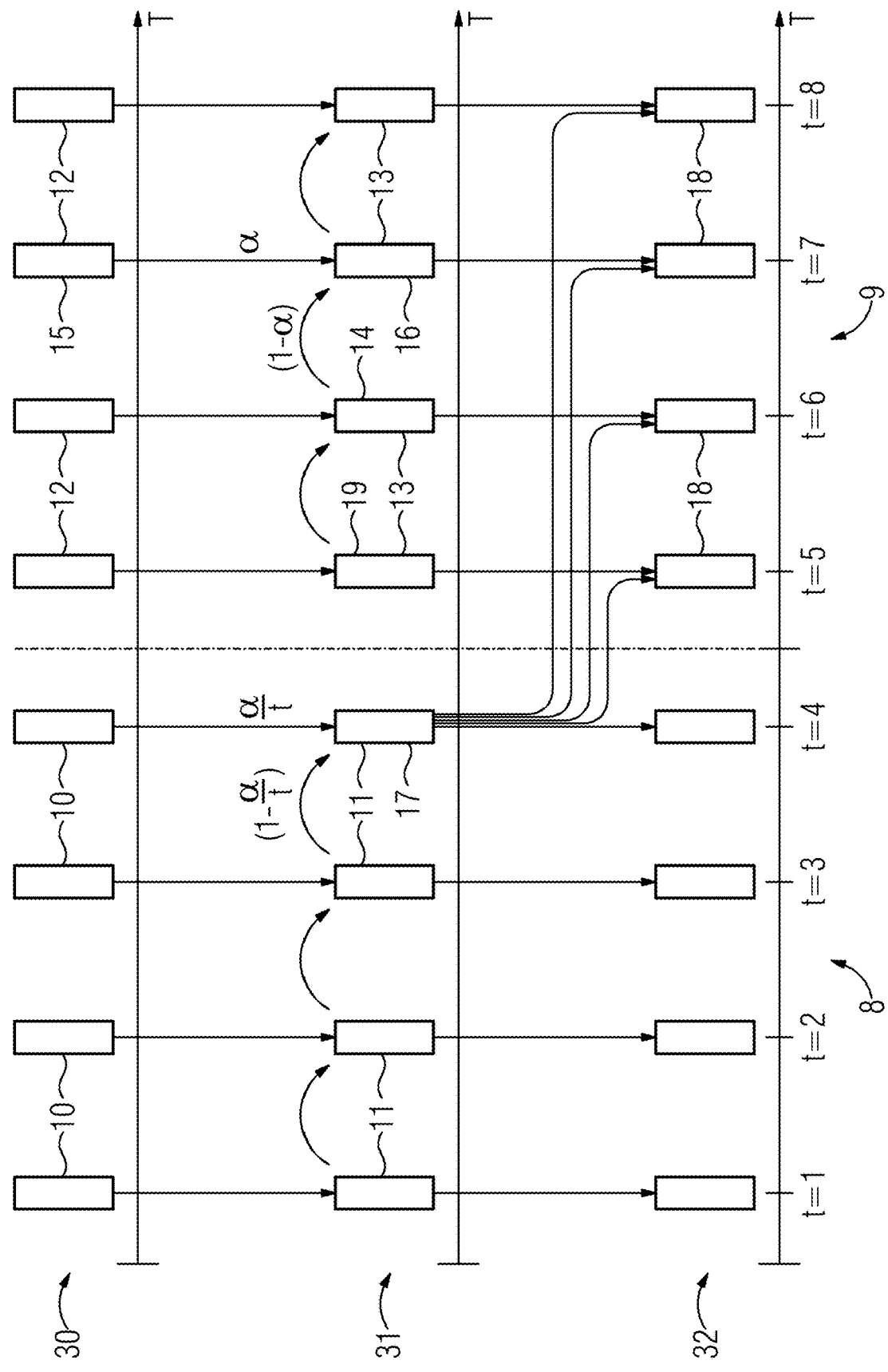
FIG. 2 depicts a schematic overview of an example of image processing by the medical X-ray device.

FIG. 2 is now intended to explain a method for operating the medical X-ray device 1 in more detail. To this end, FIG. 2 depicts an overview of multiple X-ray images in different processing acts on a time axis T. The method has a first phase 8 and a second phase 9. According to the time axis T, the first phase 8 takes place before the second phase 9. During the first phase, a plurality of first X-ray images 10 is recorded by the X-ray device 1. During the second phase 9, a plurality of second X-ray images 12 is recorded by the medical X-ray device 1. In the second phase 9, the medical X-ray device 1 may detect a movement at the body position. This movement may be due to the addition of a contrast agent to a body fluid that flows through the body region. Alternatively, the movement of a medical object, (e.g., a guidewire or a catheter), may be detected by the medical X-ray device 1. The recording of the first X-ray images 10 and second X-ray images 12 may be understood to be a first processing level 30. In the first processing level 30, the first X-ray images 10 and the second X-ray images 12 are in each case recorded individually and optionally processed individually in each case. The first X-ray images 10 and the second X-ray images 12 are recorded by the recording unit 20.

In order to increase the image quality, a respective mixing or averaging of the first X-ray images 10 and the second X-ray images 12 is provided in a second processing level 31. This averaging or mixing may reduce image noise in the images. To this end, it is possible either to improve a signal-to-noise ratio with the same dose or to reduce the dose with the same signal-to-noise ratio. It is also possible to mix the two options, e.g., the dose is reduced and simultaneously the signal-to-noise ratio increased.

In this example, the X-ray images 10 of the first phase 8 are combined iteratively to form respective mask images 11. Herein, the mask image 11 is updated or re-averaged with each newly arrived first X-ray image 10. In this example, this is performed with the following formula 1:

$$y_t^* = \frac{\alpha}{t} \cdot y_t + \left(1 - \frac{\alpha}{t}\right) \cdot y_{t-1}^* \quad (1)$$

Herein, t designates the respective number of an image on the time axis T. In other words, t may be designated as the number of the respective frame (image in an image series). $\alpha$ designates an averaging amount. In the first phase 8, $\alpha$ may be set to the value 1, because the averaging amount $\alpha$ is provided for movement-dependent averaging (see second phase 9). In other words, the first mask image 11 (t=1) is calculated according to the following formula 2:

$$y_t^* = 1 \cdot y_1 + (1-1) y_0^* \quad (2)$$

The second mask image 11 (t=2) is calculated according to following formula 3:

$$y_2^* = 1/2 \cdot y_2 + (1-1/2) y_1^* \quad (3)$$

The third mask image 11 (t=3) is calculated according to following formula 4:

$$y_3^* = 1/3 \cdot y_3 + (1-1/3) y_2^* \quad (4)$$

Herein, $y_t^*$ in each case designates one of the mask images 11 with the number t. In other words, $y_1^*$ designates the mask image 11 with the number t=1, $y_2^*$ The mask image 11 with the number t=2 and $y_3^*$ the mask image 11 with the number t=3. Accordingly, $y_{t-1}^*$ designates the respective one of the mask images 12 with a number t that is lower by 1 than that of the respective mask image 12 with the number t. $y_0^*$ would designate a previous mask image, which does not exist in the present case, but which is used in the formula to calculate the mask image 11 for t=1 because 1−1=0. $y_1$ designates the first X-ray image 10 with the number t=1, $y_2$ designates the first X-ray image 10 with the number t=2, $y_3$ designates the first X-ray image 10 with the number t=3 and $y_t$ designates an arbitrary first X-ray image 10 with the number t. Accordingly, $y_{t-1}$ designates the respective one of the first X-ray images 10 with a number t that is lower by 1 than the respective one of the X-ray images 10 with the number t.

In the present example, four first X-ray images 10 are recorded. These are averaged recursively in accordance with formula 1. Formula 1 corresponds to arithmetic averaging when $\alpha=1$. In contrast to conventional arithmetic averaging, herein however, the averaging is performed recursively; this means, on the arrival of a new first X-ray image 10, re-averaging is not performed over all the previous X-ray images 10; only the respective previous one of the X-ray images 10 is used for the averaging. The last mask image 17 of the four mask images 11 is stored at the end of phase 8 for the second phase 9.

In the second phase 9, subsequent images 13 are formed from the second X-ray images 12. Herein, averaging is performed according to a formula that may be understood similarly to formula 1. In contrast to formula 1, the following formula 5, uses the variable t=1. Hence, in principle, this relates to the same formula as for the mixing or averaging of the mask images 11. Formula 5 is as follows:

$$y_t^* = \alpha \cdot y_t + (1-\alpha) \cdot y_{t-1}^* \quad (5)$$

In formula 5, $y_t^*$ designates the respective subsequent image 13 with the number t. $y_{t-1}^*$ designates the respective subsequent image 13 with the number t-1. $y_t$ designates the respective second X-ray image 12 with the number t. The use of this formula is explained in more detail in the following by way of example with reference to a first subsequent image 14, a second X-ray image 15 and a second subsequent image 16. The first subsequent image 14 contributes to the second subsequent image 16 with the factor $(1-\alpha)$. The second X-ray image 15 contributes to second subsequent image 16 with the factor $\alpha$. In the present example, the number t of the second subsequent image 16 is t=7. Hence, in the present case, the formula for calculating the second subsequent image 16 is as follows (formula 6):

$$y_7^* = \alpha \cdot y_7 + (1-\alpha) \cdot y_6^* \quad (6)$$

In formula 6, $y_7^*$ designates the second subsequent image 16. $y_6^*$ designates the first subsequent image 14. $y_7$ designates the second X-ray image 15. The averaging amount $\alpha$ is dependent on a deviation between the first subsequent image 14 and the second X-ray image 15. With the present X-ray device, the generating unit 24 (see FIG. 1) is embodied to generate the second subsequent image 16 from the first subsequent image 14 and the second X-ray image 15 or from the second X-ray image 15.

Figure 3:
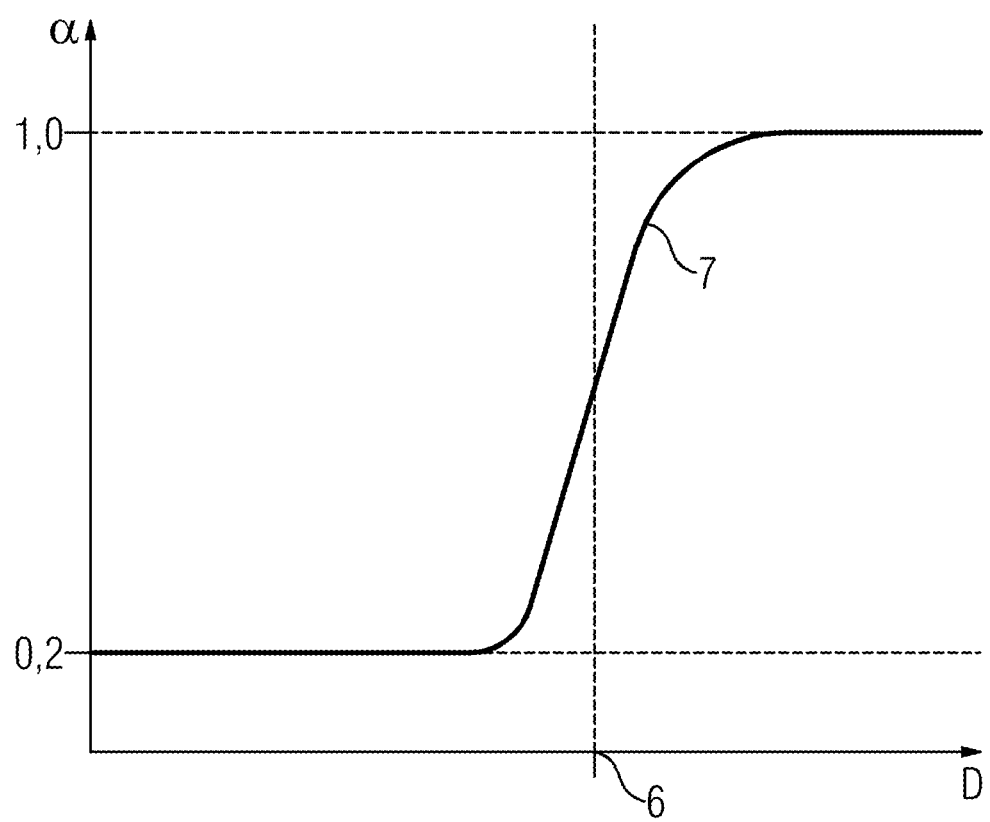
FIG. 3 depicts an example of a distribution function for an averaging amount.

For the determination of the averaging amount $\alpha$, first a degree of deviation D is determined. In the present example, the first determining unit 22 is embodied to determine the degree of deviation. For the determination of the degree of deviation, a deviation between the first subsequent image 14 and the second X-ray image 15 is determined. In the present case, the degree of deviation is determined individually for each pixel of the second X-ray image 15 or the first subsequent image 14. To this end, in each case a difference is formed between the underlying intensities or gray values of corresponding pixels of the second X-ray image 15 and the first subsequent image 14. From this, the amount of the respective difference is formed. These two acts (formation of the difference, formation of the amount) are performed for all the pixels of the subsequent image 14 and the second X-ray image 15, separately in each case. In the present example, corresponding pixels of the first subsequent image 14 and the second X-ray image 15 are pixels with the same coordinates. The respective amounts of the respective difference form the respective degree of deviation D for the respective corresponding pixels. Then, a respective averaging amount $\alpha$ is determined for each pixel of the second X-ray image 15 or the first subsequent image 14. In the present example, the second determining unit 23 of the X-ray device 1 is embodied to determine the averaging amount α in dependence on the degree of deviation D according to a predetermined rule. FIG. 3 depicts a distribution function 7, which is part of the predetermined rule for determining the averaging amount α. The distribution function 7 may be used to assign a respective value for the averaging amount α to each value of the degree of deviation D. In the present example, the averaging amount α includes a value range of 0.2 to 1. The averaging amount α takes on the value 1, the second subsequent image 16 is exclusively formed from the second X-ray image 15. As the averaging amount α falls, the proportion in which the second subsequent image 16 is formed from the first subsequent image 14 increases.

In the present example, formula 5 or formula 6 is used individually for each pixel of the second subsequent image 16. In other words, an intensity of each pixel of the second subsequent image 16 may be calculated or determined individually in each case by formula 5 or formula 6. In this way, image regions in which there is a high degree of change between the first subsequent image 14 and the second X-ray image 15 are not averaged at all or are averaged to a lesser degree than image regions in which there is a low degree of change between the first subsequent image 14 and the second X-ray image 15. Herein, a high degree of change may refer to a degree of deviation D that is greater than a predetermined threshold value 6 (see FIG. 4). A low degree of change may refer to a degree of deviation D that is lower than the predetermined threshold value 6.

In order to be able to adapt the determination of the averaging amount α particularly well to an operating state of the X-ray device 1, the distribution function 7 is selected in dependence on an operating parameter of the X-ray device 1. For example, a plurality of different distribution functions 7 for different operating states is stored in the X-ray device 1. It is then possible to select the distribution functions 7 suitable for the instantaneous operating state in dependence on a current operating parameter of the X-ray device 1. Examples of operating parameter are one or more of the following: dose, acceleration voltage, X-ray frequency to be used, body region, or physiological data (e.g., height, weight, or gender of a person to be examined) to be examined. The different distribution functions 7 may be characterized by a respective threshold value 6. The threshold value 6 may correspond to a point of inflexion of the distribution function 7. The distribution function 7 may be modeled on a step function or theta function, also called a Heaviside function. However, herein, the distribution function 7 is shifted by the threshold value 6 parallel to the x-axis or in the present case D-axis. In addition, compared to the theta function, in the present case the distribution function 7 is rounded off in the region around the step change, e.g., in the region around the threshold value 6.

Accordingly, there is a second option for the provision of the distribution function 7. For example, instead of a plurality of different distribution functions 7, a plurality of threshold values 6 and/or values for the rounding-off in the region of threshold value 6 for different values of the operating parameter is stored in the X-ray device 1. The distribution function 7 may then be formed based on the theta function taking account of the threshold value 6 and/or the measure for the rounding-off at the threshold value 6.

FIG. 2 depicts a third processing level 32. The third processing level 32 shows which X-ray images will be output by the output unit 26 for the examination. In the first phase 8, in each case the most current mask image 11, the mask image 11, may be output with the currently highest number t. In the second phase 9, in each case the most current subsequent image 13, e.g., the subsequent image 13 with the highest number t, is subtracted and the last or most current mask image 17 is output. In other words, an overall image 18 is formed from each of the subsequent images 13 by subtracting the last mask image 17. These overall images 18 are output in succession according to the time axis T. Hence, the present case relates to subtraction imaging. The combining unit 25 is embodied to form the overall images 18 by subtracting the last mask image 17 from the respective subsequent image 13.

Depending on the embodiment, it may not be possible to average a first subsequent image 19 in the phase, e.g., the first of the subsequent images 13 in the second phase 9, this means α is set to the value 1 for the calculation of the first subsequent image 19 in the phase or the last mask image 17 is used for the averaging of the first subsequent image 19 in the phase. In this example, the image noise may be improved as early as in the first subsequent image 19 in the phase and hence as early as in the first overall image 18 of the second phase 9.

The threshold value 6 may be at least partially specified by the evaluation of noise amplitudes. In other words, the threshold value 6 may be at least partially provided based on a noise amplitude in one or more X-ray images 10, 12. The threshold value 6 may be greater than the calculated noise amplitude. This enables the incorrection identification of noise as movement to be prevented.

The medical X-ray device 1 may include a movement compensating unit 27 for the provision of motion compensation in order to improve the depiction of the movement of a medical object. A change in position of the medical object between the first subsequent image 14 and the second X-ray image 15 is determined and respective object regions of the first subsequent image 14 and/or the second X-ray image 15 are mixed using the motion compensation. In the respective object regions, the medical object is detected in the first subsequent image 14 or the second X-ray image 15. First, the respective object regions may be determined in the first subsequent image 14 and the second X-ray image 15. The change in position of the medical object may be determined by comparing the coordinates of the respective object regions. The motion compensation may shift and/or rotate the object region of the first subsequent image 14 such that maximum overlapping with the object region of the second subsequent image is achieved. In the present example, this maximum overlapping is determined by the least squares method. This defines an overall degree of deviation between the respective object regions. This overall degree of deviation is reduced by shifting the object region of the first subsequent image 14 until a (e.g., absolute) minimum overall degree of deviation is achieved. The object regions may then be mixed. In other words, in a further object region, the second subsequent image 16 is generated by mixing or averaging the object region of the first subsequent image 14 and the object region of the second X-ray image 15. The further object region of the second subsequent image 16 may have the same coordinates as the object region of the second X-ray image 15. Formula 5 may be used for the mixing or averaging.

Overall, the exemplary embodiments show how the image quality may be improved compared to the prior art.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for operating a medical X-ray device when performing an X-ray examination, the method comprising:
    recording at least one first X-ray image of a body region as a mask image in a first phase of the X-ray examination before administration of a contrast agent or before a medical object is moved to the body region;
    providing a first subsequent image and recording a second X-ray image of the body region in a second phase of the X-ray examination following the first phase of the X-ray examination, wherein both the first subsequent image and the second X-ray image are images recorded after the administration of the contrast agent or after movement of the medical object to the body region, and wherein the second X-ray image represents the body region at a later recording time than the first subsequent image;
    determining a degree of deviation relating to a deviation in radiation intensity between the first subsequent image and the second X-ray image detected by a detector of the medical X-ray device;
    determining an averaging amount in dependence on the degree of deviation according to a predetermined rule;
    generating a second subsequent image from the first subsequent image together with the second X-ray image, wherein the averaging amount specifies proportions in which the first subsequent image and the second X-ray image are mixed thereby; and
    forming an overall image from the mask image and the second subsequent image.

2. The method of claim 1, wherein, during the generating of the second subsequent image, respective intensity values of corresponding pixels of the first subsequent image and the second X-ray image are mixed in dependence on the averaging amount.

3. The method of claim 1, wherein the degree of deviation characterizes a movement at the body region that occurs in a period between a recording time of the first subsequent image and a recording time of the second X-ray image.

4. The method of claim 1, wherein the averaging amount defines a proportion in which the second subsequent image corresponds to the second X-ray image.

5. The method of claim 1, wherein the averaging amount defines a proportion in which a pixel intensity of a pixel of the second subsequent image corresponds to a pixel intensity of a corresponding pixel of the second X-ray image.

6. The method of claim 1, wherein an amount of a difference in radiation intensity between pixels of the first subsequent image and the second X-ray image corresponding to respective pixel intensities is determined as the degree of deviation.

7. The method of claim 1, wherein the determining of the degree of deviation, the determining of the averaging amount, and the generating of the second subsequent image are carried out separately in each case for different regions of the second subsequent image.

8. The method of claim 1, wherein the determining of the degree of deviation, the determining of the averaging amount, and the generating of the second subsequent image are carried out separately in each case for individual pixels of different regions of the second subsequent image.

9. The method of claim 1, wherein the first subsequent image is an image formed from a further first subsequent image and a further second X-ray image, wherein both the further first subsequent image and the further second X-ray image are images recorded after the administration of the contrast agent or after movement of the medical object to the body region.

10. The method of claim 9, wherein the first subsequent image is formed by:
    providing the further first subsequent image and recording the further second X-ray image of the body region, wherein the further second X-ray image represents the body region at a later recording time than the further first subsequent image;
    determining a further degree of deviation relating to a deviation in radiation intensity between the further first subsequent image and the further second X-ray image;
    determining a further averaging amount in dependence on the further degree of deviation; and
    generating the first subsequent image from the further first subsequent image together with the further second X-ray image, wherein the further averaging amount specifies proportions in which the further first subsequent image and the further second X-ray image are mixed thereby.

11. The method of claim 10, wherein the first subsequent image is formed according to the following formula:

$$y_t^* = \alpha \cdot y_t + (1-\alpha) \cdot y_{t-1}^*$$

wherein:
    $y_t^*$ designates the first subsequent image,
    $y_{t-1}^*$ designates the further first subsequent image,
    $y_t$ designates the further second X-ray image, and
    $\alpha$ designates the further averaging amount.

12. The method of claim 1, wherein the determining of the averaging amount is performed using the predetermined rule by a distribution function, which is a function of the degree of deviation, and
    wherein the distribution function is provided in dependence on an operating parameter of the medical X-ray device.

13. The method of claim 12, further comprising:
    determining a noise amplitude in the first subsequent image, the second X-ray image, or both the first subsequent image and the second X-ray image; and
    defining a threshold value for the distribution function in dependence on the noise amplitude.

14. The method of claim 1, wherein, during the forming of the overall image, the mask image and the second subsequent image are subtracted from one another.

15. The method of claim 1, wherein, during the recording of the at least one first X-ray image, a plurality of first X-ray images is recorded and averaged according to a recurrence formula to generate the mask image.

16. The method of claim 15, wherein, during the generation of the mask image, a same formula is used to mix the plurality of first X-ray images as during the generating of the second subsequent image according to the generating of the second subsequent image for mixing the first subsequent image and the second X-ray image.

17. The method of claim 1, further comprising:
    determining a change in position of a medical object between the first subsequent image and the second X-ray image;
    mixing respective object regions of the first subsequent image, the second X-ray image, or both the first subsequent image and the second X-ray image using motion compensation; and
    detecting the medical object in the first subsequent image and the second X-ray image in the respective object regions.

18. The method of claim 1, wherein a respective radiation intensity of the first subsequent image and the second X-ray image is represented in grayscale, and
    wherein the determining of the degree of deviation between the first subsequent image and the second X-ray image is based on a comparison of a difference in gray values of the first subsequent image and the second X-ray image.

19. A medical X-ray device configured to perform an X-ray examination, the medical X-ray device comprising:
    an x-ray source and a detector configured to: record at least one first X-ray image of a body region as a mask image in a first phase of the X-ray examination before administration of a contrast agent or a medical object is moved to the body region; and record a second X-ray image of the body region in a second phase of the X-ray examination following administration of the contrast agent or movement of the medical object to the body region,
    wherein the medical X-ray device is configured to:
    provide a first subsequent image of the body region in the second phase of the X-ray examination following the first phase of the X-ray examination, wherein both the first subsequent image and the second X-ray image are images recorded following the administration of the contrast agent or following movement of the medical object to the body region, and wherein the second X-ray image represents the body region at a later recording time than the first subsequent image;
    determine a degree of deviation relating to a deviation in radiation intensity between the first subsequent image and the second X-ray image detected by the detector of the medical X-ray device;
    determine an averaging amount in dependence on the degree of deviation according to a predetermined rule;
    generate a second subsequent image from the second X-ray image or from the first subsequent image together with the second X-ray image, wherein the averaging amount specifies proportions in which the first subsequent image and the second X-ray image are to be mixed; and
    form an overall image from the mask image and the second subsequent image.

* * * * *